United States Patent [19]

Stark et al.

[11] Patent Number: 4,460,340
[45] Date of Patent: Jul. 17, 1984

[54] RECEPTACLE FOR DENTAL AMALGAM

[75] Inventors: Marvin M. Stark, Los Altos Hills; Kenneth B. Soelberg, Menlo Park; Roger B. Pelzner, San Mateo, all of Calif.

[73] Assignee: Marvin M. Stark Research Corporation, Santa Clara, Calif.

[21] Appl. No.: 459,812

[22] Filed: Jan. 21, 1983

[51] Int. Cl.³ .................................................. A61C 17/04
[52] U.S. Cl. ........................................ 433/91; 433/49
[58] Field of Search ................ 433/77, 91, 92, 93, 433/94, 95, 96, 229, 49, 50, 97; 366/602; 4/216, 217, 209 R; 131/231; 98/115 R; 55/385 R, 385 C, 385 G; 266/158, 159, 144; 269/302.1

[56] References Cited

U.S. PATENT DOCUMENTS

| 453,628 | 6/1891 | Durand | 433/96 |
|---|---|---|---|
| 602,572 | 4/1898 | Browne et al. | 433/92 |
| 1,137,482 | 4/1915 | Hanly | 433/49 |
| 1,159,206 | 11/1915 | Garhart | 366/602 |
| 1,664,419 | 4/1928 | Jackman | 433/77 |
| 1,896,951 | 2/1933 | Hahn | 98/115 R |
| 2,788,085 | 4/1957 | Waller | 131/231 |
| 3,332,089 | 7/1967 | Wilton | 4/347 |
| 3,559,961 | 2/1971 | Bergendal | 366/602 |
| 3,631,791 | 1/1972 | Harris et al. | 98/115 R |
| 3,880,061 | 4/1975 | Hensiek et al. | 98/115 R |
| 4,061,149 | 12/1977 | Raczkowski | 131/231 |
| 4,071,338 | 1/1978 | Hutter et al. | 98/115 R |
| 4,148,618 | 4/1979 | Christenson et al. | 131/231 |
| 4,197,646 | 4/1980 | Morrison | 433/97 |
| 4,213,755 | 7/1980 | Zweben | 433/49 |

FOREIGN PATENT DOCUMENTS

| 982813 | 6/1951 | France | 433/97 |
|---|---|---|---|
| 731210 | 4/1980 | U.S.S.R. | 98/115 R |

Primary Examiner—John J. Wilson
Attorney, Agent, or Firm—Lothrop & West

[57] ABSTRACT

For use in reducing atmospheric contamination by mercury vapor from an amalgam container, there is provided a rigid tube hooked over the rim of the container and open to the interior thereof. The duct is connected through a filter for taking out the noxious material to a vacuum source.

2 Claims, 1 Drawing Figure

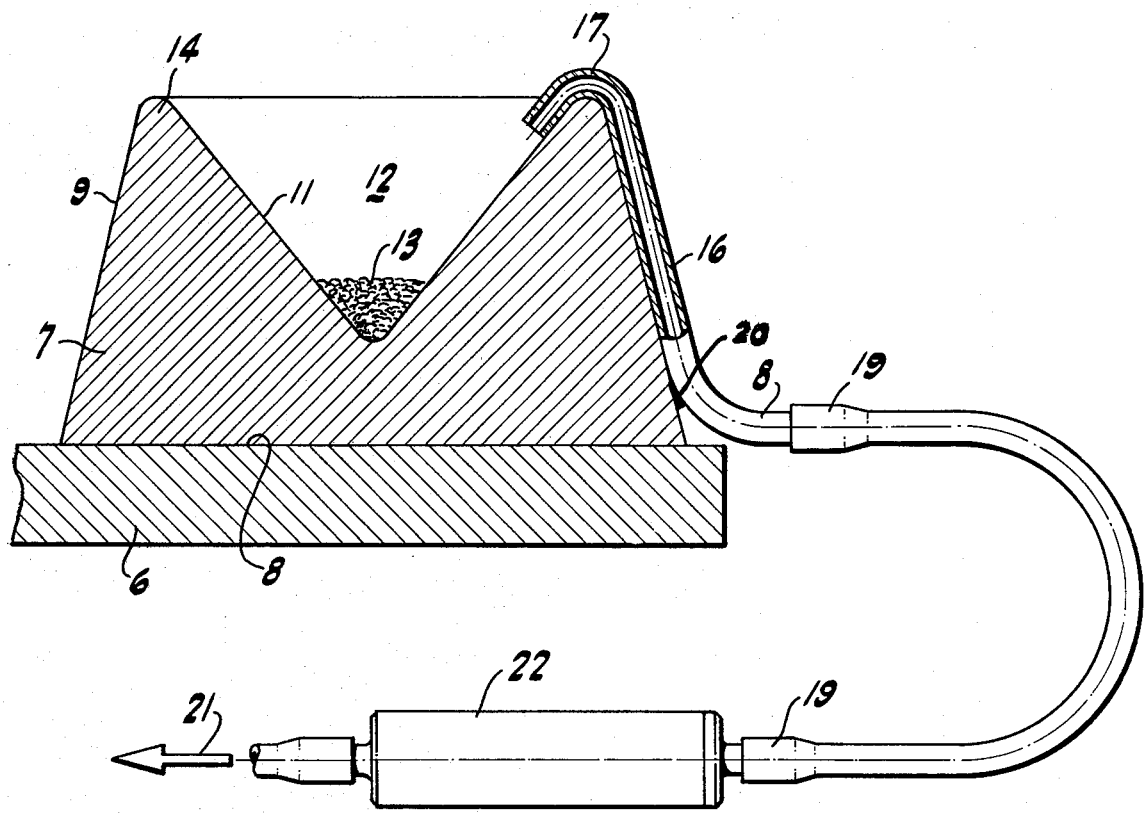

RECEPTACLE FOR DENTAL AMALGAM

BRIEF SUMMARY OF THE INVENTION

A receptacle for dental amalgam, containing mercury or the like and effective to give off noxious vapor, has an edge or rim surrounding a hollow cavity open at the top. Noxious vapor is removed from the cavity before it can disseminate into the atmosphere through a duct having an upper end hooked to engage over the rim. The duct extends partly into the cavity. The duct lies alongside and may be fastened to the side of the receptacle. At its bottom the duct is shaped to connect to a flexible tube leading to a source of vacuum. Interposed in the duct or tube is a filter to absorb the noxious vapor and retain it for subsequent disposition, leaving the air going to the vacuum pump non-toxic.

Prior Art

The applications are not aware of any prior art relating to the current disclosure.

BRIEF DESCRIPTION OF THE DRAWING

The FIGURE is a generally diagrammatic view, partially in section on a vertical transverse plane, of a dental amalgam receptacle pursuant to the invention.

DETAILED DESCRIPTION

In the practice of dentistry, it is often necessary to utilize an amalgam of materials for filling and reconstruction purposes. The amalgam almost invariably is comprised of mercury vapor or a comparable material giving off noxious or poisonous vapors. While the amount of vapor is not usually very large and does not substantially affect the patient, yet for a dentist who utilizes amalgam frequently or over a long period of time, there is an undue hazard. In order to reduce the hazard yet not interfere with the normal conduct of the dental work, we have particularly provided a dental amalgam arrangement. The device is for use on the customary dental tray 6 or any comparable support and includes an amalgam container 7. This is conveniently fabricated to have a planar base 8 and inclined, exterior conical sides 9. On the interior, the container has inclined conical sides 11 to define a cavity 12 for the reception of amalgam 13 or comparable mercury-containing materials. The container is defined between the interior cavity 12 and the exterior wall 9 by a rounded but fairly sharp circular rim 14.

Pursuant to the invention, there is provided a duct 16 usually of a stiff or rigid material formed at one end with a return bend or hook 17. This is configured to fit easily over the rim 14 and to support the duct 16 thereon. The duct 16 lies along the exterior surface 9 of the container 7 and near the bottom is configured to afford a horizontal end 18. While the duct 16 can be detachably supported by the hook 17, it can alternatively be fixed on the container 7 by an adhesive 20, or could be molded integrally with the container. Fitting over the end 18 is a flexible tube 19 leading to a source 21 of a vacuum. Interposed in the duct 19 is a filter 22 such as a charcoal filter having the effect or purpose of removing vapor from the air current flowing through the filter 22 toward the vacuum source 21.

In general operation, the receptacle 7 is disposed in its normal position on the usual table or tray 6 and remains open at the top for easy access by the dentist. Any vapor given off by the contained amalgam 13, such as mercury vapor, is not permitted to escape generally to the atmosphere. Rather, the vapor is drawn into the inlet of the tube 16 at the bend 17, the amount of air flowing into the tube 16 being sufficient in effect to sweep the upper portion of the receptacle 7 and to remove mercury vapor therefrom so that such vapor cannot discharge into the general atmosphere. The air containing noxious vapor flowing into the duct 16 is carried down through the duct 16 and around the end 18 into the tube 19 and then into the filter 22. Therein mercury vapor is condensed and retained while the accompanying air continues on, so that the discharge to the suction 21 is substantially entirely atmospheric air cleaned of noxious material.

With this arrangement, neither the patient, nor more particularly the dentist, is subjected to deleterious material emanating from the receptacle. The amount of exposure of the patient and of the dentist to noxious material is reduced substantially over prior practice.

We claim:

1. A dental amalgam device comprising an imperforate amalgam container open to the atmosphere within a top rim and adapted to contain a liquid substance emitting noxious vapor to the atmosphere from the surface of said liquid, a duct having opposite ends and at one of said ends having a return hook extending over said rim and engaged with said rim of said receptacle, said duct hook being open at said one end to the atmosphere and being positioned to be directed downwardly just above said surface within the interior of said container in position to receive noxious vapor and air, means for connecting the other of said ends of said duct to a vacuum source for passing said noxious vapor and air through said duct, and means between said other end of said duct and said vacuum source for absorbing said noxious vapor from said passing air and for discharging said air.

2. A device as in claim 1 in which said hook is in position to extend from the outside of said receptacle, over said rim and into said receptacle, and means for fastening said tube to said receptacle in said position.

* * * * *